United States Patent
Matsumoto et al.

(10) Patent No.: US 7,326,427 B2
(45) Date of Patent: Feb. 5, 2008

(54) TABLET COMPOSITION CONTAINING KAMPO MEDICINAL EXTRACT AND ITS MANUFACTURING PROCESS

(75) Inventors: Kazuhiro Matsumoto, Ibaraki (JP); Hideyuki Maruyama, Ibaraki (JP); Yoshihiko Nagano, Ibaraki (JP); Masayuki Ishimaru, Ibaraki (JP)

(73) Assignee: Tsumura & Co., Tokyo (JP)

( * ) Notice: Subject to any disclaimer, the term of this patent is extended or adjusted under 35 U.S.C. 154(b) by 0 days.

(21) Appl. No.: 10/521,016

(22) PCT Filed: Jul. 10, 2003

(86) PCT No.: PCT/JP03/08763

§ 371 (c)(1),
(2), (4) Date: Mar. 16, 2005

(87) PCT Pub. No.: WO2004/006945

PCT Pub. Date: Jan. 22, 2004

(65) Prior Publication Data

US 2005/0163868 A1 Jul. 28, 2005

(30) Foreign Application Priority Data

Jul. 12, 2002 (JP) ............................. 2002-204618

(51) Int. Cl.
*A61K 36/65* (2006.01)
*A61K 36/076* (2006.01)
*A61K 36/232* (2006.01)
*A61K 36/234* (2006.01)
*A61K 36/284* (2006.01)

(52) U.S. Cl. .................... 424/725; 424/195.15
(58) Field of Classification Search ............ None
See application file for complete search history.

(56) References Cited

U.S. PATENT DOCUMENTS 5,318,798 A * 6/1994 Uchida et al. ......... 427/213.35

FOREIGN PATENT DOCUMENTS

| JP | 56-152416 A | 11/1981 |
| JP | 61-33122 A | 2/1986 |
| JP | 11-60504 A | 3/1999 |
| WO | WO-00/37043 A1 | 6/2000 |

OTHER PUBLICATIONS

English abstract of JP 56152416 A (1981).*
English abstract of JP 61033122 A (1986).*
English abstract of JP 11060504 A (1999).*
English translation of JP 61033122.*
English translation of JP 11060504.*
English translation of JP 56152416.*
Chemical Abstracts, Aug. 10, 1959, vol. 53, No. 15, 14419h-i, 14420a AN. 1959:79551, DN:53L79551:Wensley, W.R., et al., "Release of Medication From Compressed Formulations" Canadian Pham. J., 1959, pp. 141 to 144.

* cited by examiner

*Primary Examiner*—Susan Coe Hoffman
(74) *Attorney, Agent, or Firm*—Birch, Stewart, Kolasch & Birch, LLP

(57) ABSTRACT

A Kampo medicinal extract-containing tablet composition contains a Kampo medicinal extract powder, cellulose glycolate and sodium hydrogen carbonate. It preferably further contains silicic anhydride. A process to manufacture a Kampo medicinal extract-containing tablet composition by the step of adding silicic anhydride and water to a Kampo medicinal extract powder, stirring and granulating the mixture, and the step of mixing the granulated substance with cellulose glycolate and sodium hydrogen carbonate. The Kampo medicinal extract-containing tablet composition can be satisfactorily disintegrated and dissolved and a process for manufacturing the same, by formulating specific compounds to a Kampo medicinal extract powder.

1 Claim, 4 Drawing Sheets

TABLET COMPOSITION CONTAINING KAMPO MEDICINAL EXTRACT AND ITS MANUFACTURING PROCESS

TECHNICAL FIELD

The present invention relates to a tablet composition containing a Kampo medicinal extract (Botanical medicine extract) (hereinafter also briefly referred to as "tablet composition") and to a process for manufacturing the same. More specifically, it relates to a tablet composition containing a Kampo medicinal extract which can be satisfactorily disintegrated and dissolved and to a process for manufacturing the same.

BACKGROUND ART

Tablets containing a Kampo medicinal extract powder (hereinafter also be referred to as "extract powder") are generally manufactured by a direct powder-tabletting process in which a powder mixture of a tablet composition containing a extract powder is directly tabletted to yield tablets; or by a tabletting process in which a granulated substance having a small diameter and containing a extract powder is formed, and a powder mixture of a tablet composition containing the granulated substance is then tabletted to yield tablets.

Such Kampo medicinal extract powders are highly water-absorbable, and the tablets are preferably manufactured by a manufacturing method that does not require addition of water, typically from the viewpoint of handleability in manufacturing. Accordingly, tablets containing a Kampo medicinal extract have often been manufactured by the direct powder-tabletting process in which a powder mixture is directly tabletted.

In these tablets manufactured by the direct powder tabletting process, however, the Kampo medicinal extract powder is bound firmly, water does not permeate satisfactorily and a general disintegrator with swelling property does not work effectively. It takes a long time for the tablets to disintegrate and the active ingredients do not dissolve satisfactorily. Thus, tablets superb in practical use have not yet been obtained.

To solve this problem, attempts have been made, for example, to reduce the content of the extract powder in the tablets or to add large quantities of, for example, a vehicle (excipient), a disintegrator and/or a binder. However, these techniques invite tablets with larger sizes or higher manufacturing cost due to expensive disintegrators. Certain tablets comprising sodium hydrogen carbonate so as to improve dissolution properties are known, but they do not yet show sufficient advantages.

In the process of making tablets via a granulated substance, the granulated substances containing a Kampo medicinal extract powder is manufactured typically by dry pulverization-granulation, wet extrusion-granulation or fluidized-bed granulation. However, the Kampo medicinal extract powder is highly water-absorbable as described above, and extract powder becomes firmly bound and often forms large aggregates when water is added in these processes. Therefore, the manufacturing of granulated substance requires sophisticated techniques typically to control the amount and rate of the addition of water precisely and facilities therefor. In addition, the wet extrusion granulation carries a problem of a residual solvent in final preparation products, because this technique uses an organic solvent such as ethanol. The fluidized-bed granulation invites a longer manufacturing time period, because the water content of the granulated substance must be controlled within a narrow range during granulation.

Accordingly, an object of the present invention is to solve the above problems, to improve the disintegration and dissolution properties of tablets containing a Kampo medicinal extract powder and to provide a tablet composition containing a Kampo medicinal extract which can be disintegrated and dissolved satisfactorily, and a process for manufacturing the same.

DISCLOSURE OF INVENTION

After intensive investigations to achieve the above objects, the present inventors have found that a tablet composition having improved disintegration and dissolution properties can be prepared by formulating specific compounds into a Kampo medicinal extract powder. The present invention has been accomplished based on these findings.

Specifically, to solve the above problems, the present invention provides a tablet composition containing Kampo medicinal extract which contains a Kampo medicinal extract powder, cellulose glycolate and sodium hydrogen carbonate.

In addition, the present invention provides a process for manufacturing a tablet composition containing Kampo medicinal extract, which includes the step of adding silicic anhydride and water to a Kampo medicinal extract powder, stirring and granulating the mixture, and the step of mixing the granulated substance with cellulose glycolate and sodium hydrogen carbonate to thereby manufacture the above-mentioned tablet composition containing Kampo medicinal extract.

BEST MODE FOR CARRYING OUT THE INVENTION

Figure 1:
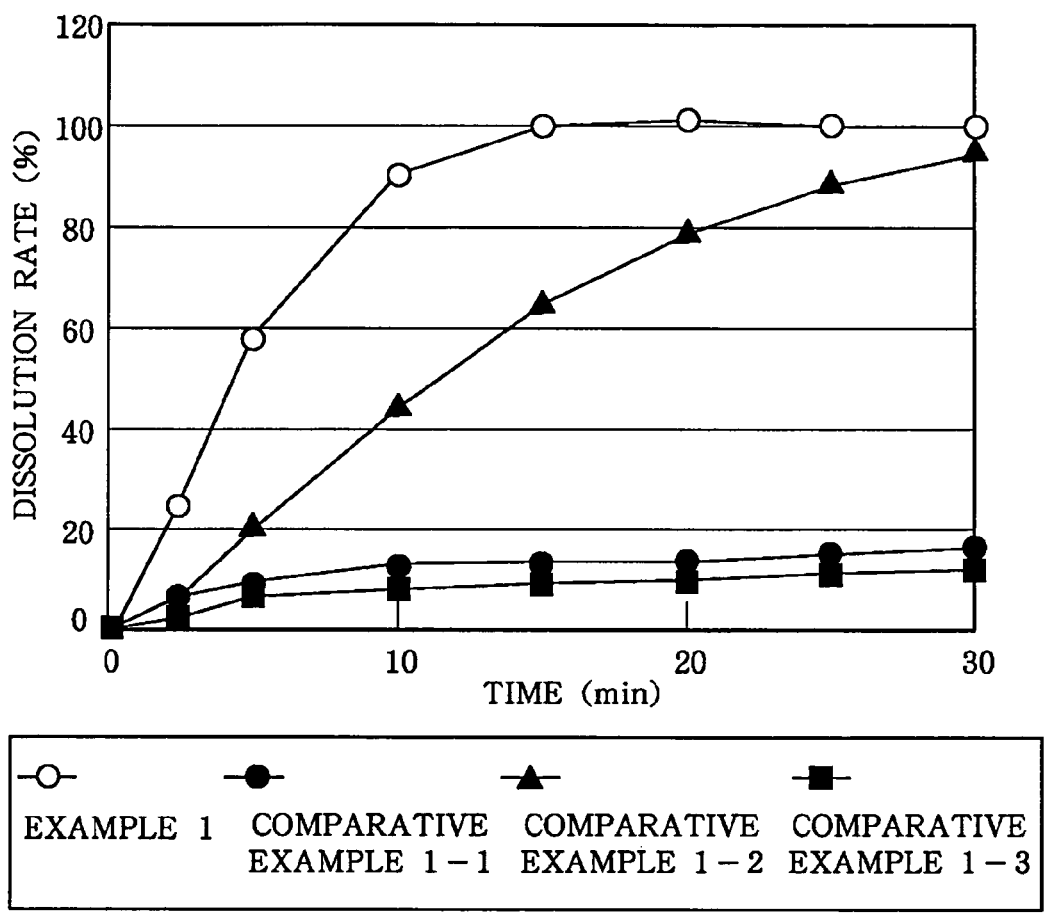
FIG. 1 shows dissolution curves of tablets according to Example 1 and Comparative Examples 1-1, 1-2 and 1-3.

The concrete embodiments of the present invention will be illustrated in detail below.

The Kampo medicinal extract powder used in the present invention is one obtained by decocting a general Kampo medicinal formulation and concentrating and drying the decoction. Examples thereof include, but are not limited to, extract powders of Kakkon-to, Kakkon-to-ka-senkyu-shin'i, Otsuji-to, Anchu-san, Hachimi-jio-gan, Dai-saiko-to, Sho-saiko-to, Saiko-keishi-to, Saiko-keishi-kankyo-to, Oren-ge-doku-to, Sho-seiryu-to, Boi-ogi-to, Toki-shakuyaku-san, Kami-shoyo-san, Keishi-bukuryo-gan, Keishi-ka-ryukotsu-borei-to, Mao-to, Bakumondo-to, Ninjin-to, Byakko-ka-nin-jin-to, Chorei-to, Hochu-ekki-to, Rikkunshi-to, Choto-san, Bofu-tsusho-san, Daio-kanzo-to, Sho-kenchu-to, Dai-ken-chu-to, Gosha-jinki-gan, Ninjin-yoei-to, San'o-shashin-to, Sairei-to, Oren-to, Toki-kenchu-to, Mashinin-gan, Mao-bushi-saishin-to, Keishi-ka-shakuyaku-daio-to and Kikyo-to. They also include herbal drug extract powders of medicines obtained by decocting one or more of crude drugs and concentrating and drying the decoction.

Carboxymethyl cellulose with a degree of etherification of 0.4 to 0.6 is suitably used as the cellulose glycolate in the present invention. The amount of the cellulose glycolate is preferably 1 to 50 parts by weight and more preferably 10 to 40 parts by weight to 100 parts by weight of the Kampo medicinal extract powder. If the amount of the cellulose glycolate is less than 1 part by weight, the advantages of the present invention to improve the disintegration and dissolution properties may be insufficient. In contrast, if it exceeds 50 parts by weight, further advantages may not be expected.

The amount of sodium hydrogen carbonate is preferably 1 to 50 parts by weight and more preferably 5 to 30 parts by weight to 100 parts by weight of the Kampo medicinal extract powder. If the amount of sodium hydrogen carbonate is less than 1 part by weight, the advantages of the present invention to improve the disintegration and dissolution properties may be insufficient. In contrast, if it exceeds 50 parts by weight, further advantages may not be expected.

The tablet composition may further comprise, for example, vehicles (excipients), binders, fluidizing agents and lubricants according to necessity. These additives include sugars and sugar alcohols such as lactose, corn starch, maltose and mannitol; starch and derivatives thereof such as corn starch, dextrin and gelatinized starch; cellulose and derivatives thereof such as crystalline cellulose and hydroxypropylcellulose; and inorganic substances such as synthesized aluminum silicate, calcium phosphate, magnesium stearate, calcium stearate and talc.

To manufacture the tablet composition of the present invention by the direct powder tabletting process, a Kampo medicinal extract powder is mixed with cellulose glycolate and sodium hydrogen carbonate and the mixture is tabletted to yield tablets. The tabletting procedure is not specifically limited and can be carried out by using a general tabletting machine.

To manufacture the tablet composition of the present invention by the wet granulation process, it is preferred that silicic anhydride and water are added to a Kampo medicinal extract powder and the mixture is stirred and granulated before the addition of cellulose glycolate and sodium hydrogen carbonate. Thus, the tablet composition can have improved disintegration and dissolution properties. The stirring and granulation procedure can be carried out in a high-speed mixer-granulator while adding dropwise or spraying water. The resulting granulated substance is then subjected to general drying and particle-size regulation procedures, cellulose glycolate and sodium hydrogen carbonate are added thereto and the mixture is tabletted. Thus, the tablet composition of the present invention can be provided.

The amount of the silicic anhydride to the Kampo medicinal extract powder is preferably 25 to 100 parts by weight to 100 parts by weight of the Kampo medicinal extract powder. If the amount of the silicic anhydride is excessively small, the disintegration and dissolution properties of the resulting tablets are not effectively improved. If it is excessively large, the tablets become upsized and invite higher manufacturing cost. Accordingly, the amount is more preferably 30 to 50 parts by weight.

A binder may be added to water for use in granulation. Examples of the binder is hydroxypropylcellulose, hydroxypropylmethylcellulose, macrogol (polyethylene glycol) and polyvinylpyrrolidone. The binder can be added as an aqueous solution of thereof by dissolving or dispersing in water.

The amount of water or the aqueous solution of binder is preferably 30 to 70 parts by weight to 100 parts by weight of the Kampo medicinal extract powder. Water or the aqueous solution of binder may be added to the extract powder dropwise or by spraying from above. More preferably, it is added by spraying continuously to yield a granulated substance having a uniform particle size.

The granulation time is generally 3 to 30 minutes. Thus, a granulated substance in the form of fine granule and/or granule is prepared. The prepared granulated substance is then subjected to drying and particle-size regulation. It can be subjected to drying and particle-size regulation under any conditions, and a general drier and particle size selector can be used. The granulation procedure is not specifically limited and a conventional procedure such as wet granulation can be appropriately employed.

The resulting granulated substance is then mixed with cellulose glycolate and sodium hydrogen carbonate and the mixture is tabletted to thereby yield tablets. The mixture can be tabletted according to any procedure, and a general tabletting machine can be employed.

In any of the above manufacturing processes, the suitable amounts of cellulose glycolate and sodium hydrogen carbonate to the Kampo medicinal extract powder can be appropriately set within the above-mentioned ranges, and other additives such as vehicles (excipients), binders, fluidizing agents and lubricants can be appropriately added according to necessity as described above.

The present invention will be illustrated in further detail with reference to several examples below.

EXAMPLE 1

| | |
|---|---|
| Toki-shakuyaku-san extract powder | 100.0 parts by weight |
| Carboxymethyl cellulose (Cellulose glycolate) | 31.7 parts by weight |
| Sodium hydrogen carbonate | 14.9 parts by weight |
| Magnesium stearate | 1.5 parts by weight |
| Light silicic anhydride | 0.4 part by weight |

The above raw materials were mixed and thereby yielded a powder mixture for tabletting. This was tabletted using a tabletting machine and thereby yielded tablets with a weight of 330 mg.

Comparative Example 1-1

| | |
|---|---|
| Toki-shakuyaku-san extract powder | 100.0 parts by weight |
| Crystalline cellulose | 47.0 parts by weight |
| Magnesium stearate | 1.5 parts by weight |

The above raw materials were mixed and thereby yielded a powder mixture for tabletting. This was tabletted using a tabletting machine and thereby yielded tablets with a weight of 330 mg.

Comparative Example 1-2

| | |
|---|---|
| Toki-shakuyaku-san extract powder | 100.0 parts by weight |
| Crystalline cellulose | 32.2 parts by weight |
| Sodium hydrogen carbonate | 14.9 parts by weight |
| Magnesium stearate | 1.5 parts by weight |

The above raw materials were mixed and thereby yielded a powder mixture for tabletting. This was tabletted using a tabletting machine and thereby yielded tablets with a weight of 330 mg.

Comparative Example 1-3

| | |
|---|---|
| Toki-shakuyaku-san extract powder | 100.0 parts by weight |
| Carboxymethyl cellulose | 31.7 parts by weight |
| Crystalline cellulose | 15.3 parts by weight |
| Magnesium stearate | 1.5 parts by weight |

The above raw materials were mixed and thereby yielded a powder mixture for tabletting. This was tabletted using a tabletting machine and thereby yielded tablets with a weight of 330 mg.

EXAMPLE 2

| | |
|---|---|
| Kami-shoyo-san extract powder | 100.0 parts by weight |
| Carboxymethyl cellulose | 31.7 parts by weight |
| Sodium hydrogen carbonate | 14.9 parts by weight |
| Magnesium stearate | 1.5 parts by weight |
| Light silicic anhydride | 0.4 part by weight |

The above raw materials were mixed and thereby yielded a powder mixture for tabletting. This was tabletted using a tabletting machine and thereby yielded tablets with a weight of 380 mg.

Comparative Example 2

| | |
|---|---|
| Kami-shoyo-san extract powder | 100.0 parts by weight |
| Crystalline cellulose | 47.0 parts by weight |
| Magnesium stearate | 1.5 parts by weight |

The above raw materials were mixed and thereby yielded a powder mixture for tabletting. This was tabletted using a tabletting machine and thereby yielded tablets with a weight of 380 mg.

EXAMPLE 3

| | |
|---|---|
| Keishi-bukuryo-gan extract powder | 100.0 parts by weight |
| Carboxymethyl cellulose | 25.1 parts by weight |
| Crystalline cellulose | 23.2 parts by weight |
| Sodium hydrogen carbonate | 16.7 parts by weight |
| Magnesium stearate | 1.7 parts by weight |
| Light silicic anhydride | 0.5 part by weight |

The above raw materials were mixed and thereby yielded a powder mixture for tabletting. This was tabletted using a tabletting machine and thereby yielded tablets with a weight of 330 mg.

Comparative Example 3

| | |
|---|---|
| Keishi-bukuryo-gan extract powder | 100.0 parts by weight |
| Crystalline cellulose | 65.6 parts by weight |
| Magnesium stearate | 1.7 parts by weight |

The above raw materials were mixed and thereby yielded a powder mixture for tabletting. This was tabletted using a tabletting machine and thereby yielded tablets with a weight of 330 mg.

EXAMPLE 4

Using a high-speed mixer-granulator, 100 parts by weight of Daio-kanzo-to extract powder and 30 parts by weight of light silicic anhydride were granulated while adding 50 parts by weight of water by spraying. The granulation time was set at 10 minutes. Subsequently, drying and particle size regulation were carried out to thereby yield a granulated substance. A vertical granulator Model FM-VG-25 (product of Powrex Co., Ltd.) was used as the high-speed mixer-granulator. The same shall apply hereinafter.

| | |
|---|---|
| Above-prepared granulated substance | 130 parts by weight |
| Carboxymethyl cellulose | 39 parts by weight |
| Sodium hydrogen carbonate | 9 parts by weight |
| Magnesium stearate | 2 parts by weight |

The above raw materials were mixed and thereby yielded a powder mixture for tabletting. This was tabletted using a tabletting machine and thereby yielded tablets with a weight of 300 mg.

Comparative Example 4-1

| | |
|---|---|
| Daio-kanzo-to extract powder | 100 parts by weight |
| Crystalline cellulose | 78 parts by weight |
| Magnesium stearate | 2 parts by weight |

The above raw materials were mixed and thereby yielded a powder mixture for tabletting. This was tabletted using a tabletting machine and thereby yielded tablets with a weight of 300 mg.

Comparative Example 4-2

| | |
|---|---|
| Granulated substance of Example 4 | 130 parts by weight |
| Crystalline cellulose | 48 parts by weight |
| Magnesium stearate | 2 parts by weight |

The above raw materials were mixed and thereby yielded a powder mixture for tabletting. This was tabletted using a tabletting machine and thereby yielded tablets with a weight of 300 mg.

Comparative Example 4-3

| | |
|---|---|
| Granulated substance of Example 4 | 130 parts by weight |
| Crystalline cellulose | 39 parts by weight |
| Sodium hydrogen carbonate | 9 parts by weight |
| Magnesium stearate | 2 parts by weight |

The above raw materials were mixed and thereby yielded a powder mixture for tabletting. This was tabletted using a tabletting machine and thereby yielded tablets with a weight of 300 mg.

Comparative Example 4-4

| | |
|---|---|
| Granulated substance of Example 4 | 130 parts by weight |
| Carboxymethyl cellulose | 39 parts by weight |
| Crystalline cellulose | 9 parts by weight |
| Magnesium stearate | 2 parts by weight |

The above raw materials were mixed and thereby yielded a powder mixture for tabletting. This was tabletted using a tabletting machine and thereby yielded tablets with a weight of 300 mg.

EXAMPLE 5

Using the high-speed mixer-granulator, 100 parts by weight of Kakkon-to extract powder and 30 parts by weight of light silicic anhydride were granulated while adding 48 parts by weight of water by spraying. The granulation time was set at 10 minutes. Subsequently, drying and particle size regulation were carried out to thereby yield a granulated substance.

| | |
|---|---|
| Above-prepared granulated substance | 130 parts by weight |
| Carboxymethyl cellulose | 21 parts by weight |
| Sodium hydrogen carbonate | 8 parts by weight |
| Magnesium stearate | 2 parts by weight |

The above raw materials were mixed and thereby yielded a powder mixture for tabletting. This was tabletted using a tabletting machine and thereby yielded tablets with a weight of 380 mg.

Comparative Example 5

| | |
|---|---|
| Kakkon-to extract powder | 100 parts by weight |
| Crystalline cellulose | 59 parts by weight |
| Magnesium stearate | 2 parts by weight |

The above raw materials were mixed and thereby yielded a powder mixture for tabletting. This was tabletted using a tabletting machine and thereby yielded tablets with a weight of 380 mg.

EXAMPLE 6

Using the high-speed mixer-granulator, 100 parts by weight of Saiko-keishi-to extract powder and 30 parts by weight of light silicic anhydride were granulated while adding 53 parts by weight of water by spraying. The granulation time was set at 10 minutes. Subsequently, drying and particle size regulation were carried out to thereby yield a granulated substance.

| | |
|---|---|
| Above-prepared granulated substance | 130 parts by weight |
| Carboxymethyl cellulose | 26 parts by weight |
| Sodium hydrogen carbonate | 8 parts by weight |
| Magnesium stearate | 2 parts by weight |

The above raw materials were mixed and thereby yielded a powder mixture for tabletting. This was tabletted using a tabletting machine and thereby yielded tablets with a weight of 380 mg.

Comparative Example 6

| | |
|---|---|
| Saiko-keishi-to extract powder | 100 parts by weight |
| Crystalline cellulose | 65 parts by weight |
| Magnesium stearate | 2 parts by weight |

The above raw materials were mixed and thereby yielded a powder mixture for tabletting. This was tabletted using a tabletting machine and thereby yielded tablets with a weight of 380 mg.

The tablets prepared according to Examples 1 to 6 and Comparative Examples 1-1 to 6 were subjected to disintegration test according to the disintegration test method specified in the Japanese Pharmacopoeia. Using purified water at 37° C. as a test medium, the time period until a tablet disintegrated was determined. The disintegration time periods of six tablets of each sample were determined, and the average thereof was calculated.

The test results are shown in Table 1 below.

TABLE 1

| Tablet of Example | Disintegration time (min) | Tablet of Comparative Example | Disintegration time (min) |
|---|---|---|---|
| Example 1 | 15 | Comp. Ex. 1-1 | 65 |
| | | Comp. Ex. 1-2 | 31 |
| | | Comp. Ex. 1-3 | 55 |
| Example 2 | 10 | Comp. Ex. 2 | 58 |
| Example 3 | 9 | Comp. Ex. 3 | 41 |
| Example 4 | 11 | Comp. Ex. 4-1 | 73 |
| | | Comp. Ex. 4-2 | 80 |
| | | Comp. Ex. 4-3 | 46 |
| | | Comp. Ex. 4-4 | 40 |
| Example 5 | 10 | Comp. Ex. 5 | 68 |
| Example 6 | 10 | Comp. Ex. 6 | 82 |

Next, the tablets according to Examples 1 to 6 and Comparative Examples 1-1 to 6 were subjected to dissolution test. The dissolution test was carried out according to Method 2 (paddle method) of the dissolution test method specified in the Japanese Pharmacopoeia under the following conditions.

Test medium: purified water
Amount of test medium: 900 mL
Temperature of medium: 37° C.
Paddle rotation speed: 50 $min^{-1}$
Detector: UV (ultraviolet ray)

Figure 2:
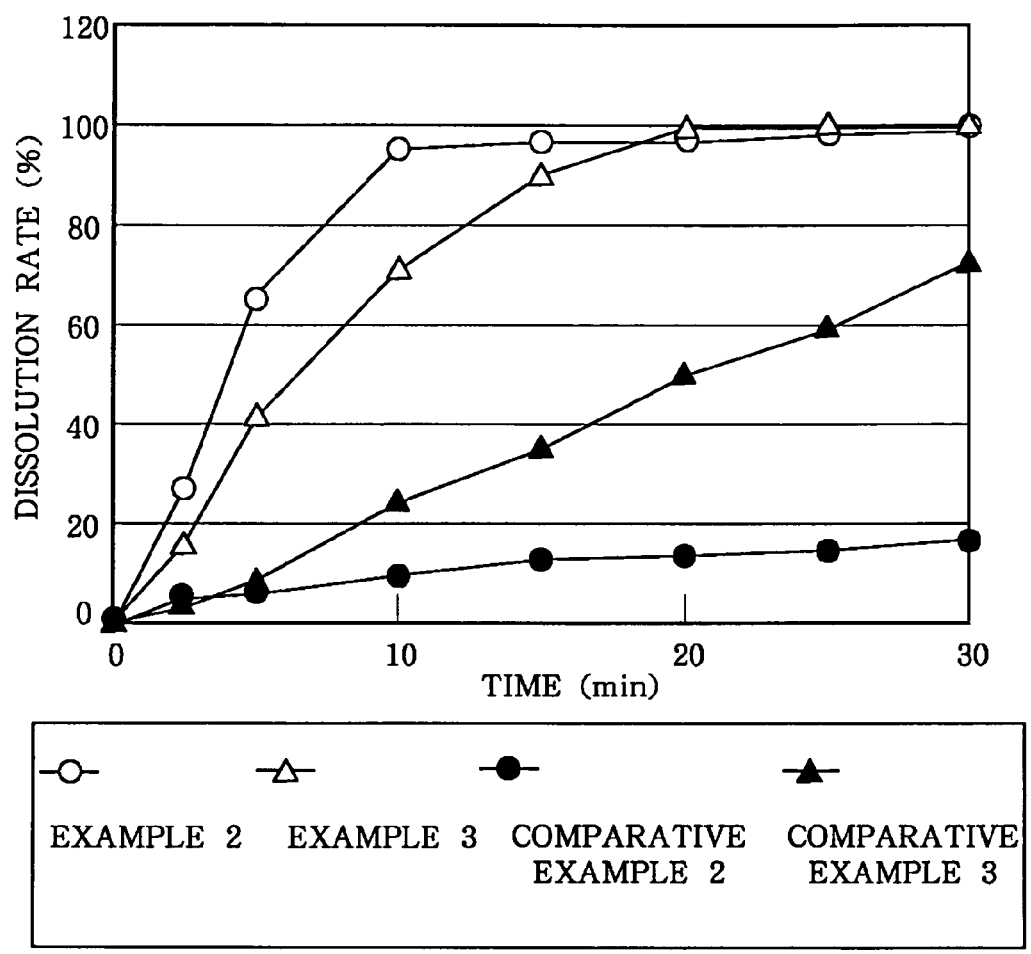
FIG. 2 shows dissolution curves of tablets according to Examples 2 and 3, and Comparative Examples 2 and 3.
Figure 3:
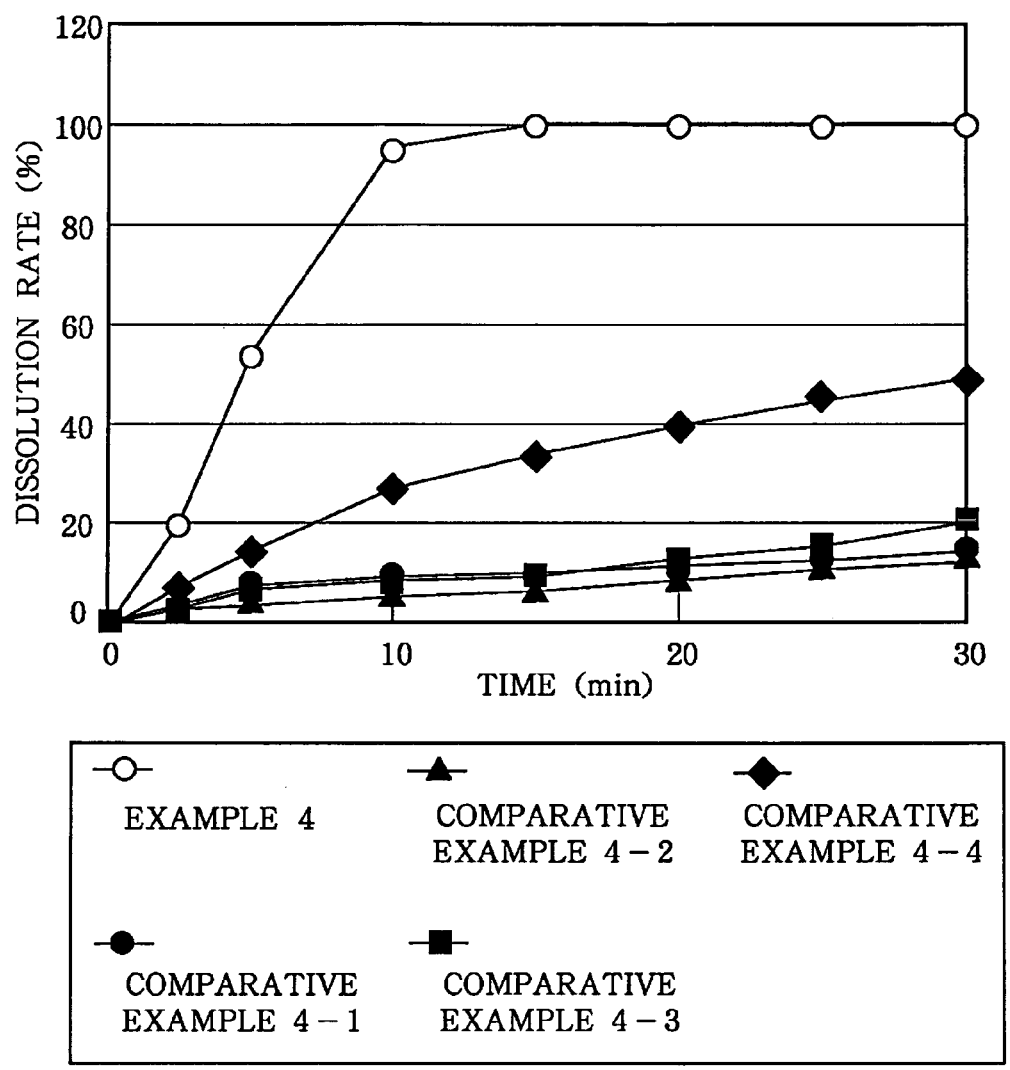
FIG. 3 shows dissolution curves of tablets according to Example 4, and Comparative Examples 4-1, 4-2, 4-3 and 4-4.
Figure 4:
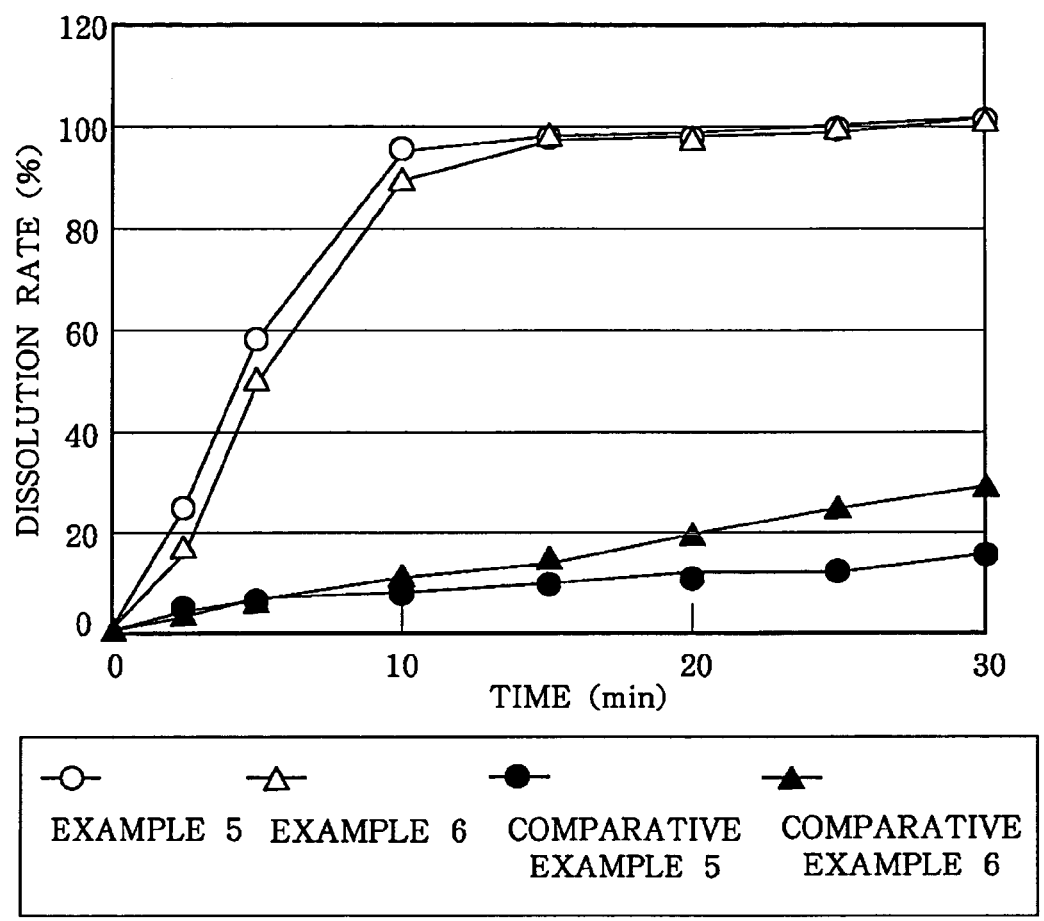
FIG. 4 shows dissolution curves of tablets according to Examples 5 and 6, and Comparative Examples 5 and 6.

The results of the dissolution test are shown in Table 2 below. There are shown dissolution curves of Example 1 and Comparative Examples 1-1, 1-2 and 1-3 in FIG. 1, dissolution curves of Examples 2 and 3 and Comparative Examples 2 and 3 in FIG. 2, dissolution curves of Example 4 and Comparative Examples 4-1, 4-2, 4-3 and 4-4 in FIG. 3, and dissolution curves of Examples 5 and 6 and Comparative Examples 5 and 6 in FIG. 4, respectively.

TABLE 2

| Tablets of Example and Comparative Example | Dissolution rate (%) | | | |
|---|---|---|---|---|
| | 5 min | 10 min | 20 min | 30 min |
| Example 1 | 58 | 90 | 101 | 100 |
| Comp. Ex. 1-1 | 8 | 11 | 14 | 17 |
| Comp. Ex. 1-2 | 22 | 45 | 79 | 97 |
| Comp. Ex. 1-3 | 5 | 6 | 10 | 13 |
| Example 2 | 65 | 93 | 98 | 99 |
| Comp. Ex. 2 | 7 | 9 | 12 | 17 |
| Example 3 | 42 | 72 | 99 | 100 |
| Comp. Ex. 3 | 9 | 24 | 49 | 72 |
| Example 4 | 53 | 96 | 100 | 100 |
| Comp. Ex. 4-1 | 6 | 9 | 13 | 16 |
| Comp. Ex. 4-2 | 4 | 6 | 11 | 14 |
| Comp. Ex. 4-3 | 5 | 8 | 14 | 21 |
| Comp. Ex. 4-4 | 16 | 26 | 39 | 49 |
| Example 5 | 59 | 94 | 98 | 99 |

TABLE 2-continued

| Tablets of Example and Comparative Example | Dissolution rate (%) | | | |
|---|---|---|---|---|
| | 5 min | 10 min | 20 min | 30 min |
| Comp. Ex. 5 | 6 | 8 | 12 | 15 |
| Example 6 | 50 | 89 | 99 | 100 |
| Comp. Ex. 6 | 5 | 10 | 19 | 28 |

INDUSTRIAL APPLICABILITY

As is described above, the present invention can provide a tablet composition containing Kampo medicinal extract which can be satisfactorily disintegrated and dissolved and a process for manufacturing the same, by formulating specific compounds to a Kampo medicinal extract powder.

The invention claimed is:
1. A tablet composition, comprising:

| | |
|---|---|
| Toki-shakuyaku-san extract powder | 100.0 parts by weight, |
| Carboxymethyl cellulose (cellulose glycolate) | 37.1 parts by weight, |
| Sodium hydrogen carbonate | 14.9 parts by weight, |
| Magnesium stearate | 1.5 parts by weight, and |
| Light silicic anhydride | 0.4 parts by weight. |

* * * * *